(12) United States Patent
Lee et al.

(10) Patent No.: US 6,617,477 B2
(45) Date of Patent: Sep. 9, 2003

(54) PROCESS FOR PREPARING 1,3-ALKANEDIOLS FROM 3-HYDROXYESTERS

(75) Inventors: Byeong No Lee, Seoul (KR); Eun Joo Jang, Daejun-Shi (KR); Jung Ho Lee, Daejun-Shi (KR); Hyung Rok Kim, Daejun-Shi (KR); Yo Han Han, Daejun-Shi (KR); Hyun Kwan Shin, Daejun-Shi (KR); Ho Sun Lee, Chungnam-do (KR)

(73) Assignees: Samsung Electronics Co., Ltd., Kyungki-do (KR); Korea Research Institute of Chemical Technology, Daejun-Shi (KR)

( * ) Notice: Subject to any disclaimer, the term of this patent is extended or adjusted under 35 U.S.C. 154(b) by 0 days.

(21) Appl. No.: 09/995,798

(22) Filed: Nov. 29, 2001

(65) Prior Publication Data

US 2002/0161268 A1 Oct. 31, 2002

(30) Foreign Application Priority Data

Nov. 29, 2000 (KR) .......................... 2000-71643
Jun. 13, 2001 (KR) .......................... 2001-33142

(51) Int. Cl.$^7$ .......................... C07C 27/00; C07C 27/04; C07C 31/18; C07C 29/00
(52) U.S. Cl. .......................... 568/864; 568/861
(58) Field of Search .......................... 568/864, 861

(56) References Cited

U.S. PATENT DOCUMENTS

| | | | |
|---|---|---|---|
| 4,440,873 A | 4/1984 | Miyazaki et al. | 502/244 |
| 4,443,649 A | 4/1984 | Jones et al. | 585/500 |
| 4,511,744 A | 4/1985 | Miyazaki et al. | 568/864 |
| 4,929,777 A | 5/1990 | Irick et al. | 568/864 |
| 4,973,769 A | 11/1990 | Mueller et al. | 568/864 |
| 5,093,537 A | 3/1992 | Unrub et al. | 368/862 |
| 5,185,476 A | 2/1993 | Gustafson | 568/831 |
| 5,406,004 A | 4/1995 | Eastland et al. | 568/831 |
| 5,723,389 A | 3/1998 | Slaugh et al. | 468/862 |
| 5,731,478 A | 3/1998 | Slaugh | 568/862 |
| 5,770,776 A | 6/1998 | Powell et al. | 568/862 |
| 5,777,182 A | 7/1998 | Powell | 568/862 |
| 5,821,092 A | 10/1998 | Nagarajan | |
| 6,013,494 A | 1/2000 | Nakamura | |
| 6,136,576 A | 10/2000 | Diaz-Torres | |
| 6,140,543 A | 10/2000 | Brossmer et al. | |
| 6,191,321 B1 | 2/2001 | Forschner et al. | |
| 6,232,511 B1 | 5/2001 | Haas | |

FOREIGN PATENT DOCUMENTS

| | | |
|---|---|---|
| DE | 3734764 | 5/1989 |
| EP | 0361082 | 4/1990 |
| EP | 0373946 | 6/1990 |
| EP | 0577972 | 1/1994 |
| WO | 99/38613 | 8/1999 |
| WO | 00/18712 | 4/2000 |

*Primary Examiner*—Johann Richter
*Assistant Examiner*—Elvis O. Price
(74) *Attorney, Agent, or Firm*—Lee & Sterba, P.C.

(57) ABSTRACT

A process for preparing an 1,3-alkanediol from a 3-hydroxyester includes hydrogenating a 3-hydroxyester in an alcohol-containing solvent in the presence of a hydrogenation catalyst prepared by adding an alkaline precipitator to an aqueous solution containing a copper salt to form particles, and then aging the particles following addition of colloidal silica thereto. Novel hydrogenation catalysts so prepared are also disclosed.

19 Claims, No Drawings

PROCESS FOR PREPARING 1,3-ALKANEDIOLS FROM 3-HYDROXYESTERS

BACKGROUND OF THE INVENTION

1. Field of the Invention

The present invention relates to a process for preparing 1,3-alkanediols from 3-hydroxyesters. More specifically, the present invention relates to a hydrogenation catalyst for preparation of 1,3-alkanediols from 3-hydroxyesters in a high yield as well as a process for preparing 1,3-alkanediols by hydrogenating 3-hydroxyesters in the presence of the catalyst.

2. Description of the Prior art 1,3-alkanediols have been widely used as coating materials or intermediates for various organic syntheses as well as raw materials for production of polyesters. At present, several processes are known for preparing 1,3-alkanediols. For example, a process for preparing 1,3-alkanediols by hydroformylating epoxides into 3-hydroxyaldehyde derivatives and then hydrogenating the 3-hydroxyaldehyde derivatives has been used (See U.S. Pat. Nos. 5,770,776; 5,723,389; 5,731,478; and 5,777,182). Further, a process for preparing 1,3-alkanediols by hydrating acrolein into 3-hydroxypropanal and then hydrogenating the resulting 3-hydroxypropanal has been also used (see European Patent No. 577,972; U.S. Pat. No. 5,093,537). In addition to the above processes, another method has been reported to provide 1,3-alkanediols through a certain biological reaction, wherein glycerol is used as a starting material (see European Patent No. 361,082; German Patent No. 3,734,764).

On the other hand, Shell Co. has commercially produced 1,3-propanediol through hydrogenation of 3-hydroxypropanal, which is prepared by hydroformylation of ethylene oxides. However, this process has disadvantages in that the unstable 3-hydroxypropanal is likely to oligomerize itself and many other side products including acetal are produced. Thus, hydrogenation into 1,3-propanediol cannot be properly completed, and the quality of the final product is lowered.

Even though an alternative process was suggested, wherein 1,3-alkanediols are prepared by carboesterifying epoxides with carbon monoxides and alcohols to produce 3-hydroxyesters, and then hydrogenating the ester groups of the 3-hydroxyesters, it has not been put to practical use in the industrial field. This is because the reaction pathway thereof is very unselective for producing 1,3-alkanediols from 3-hydroxyesters when a conventional hydrogenation catalyst, such as copper-chromium oxide, copper-zinc oxide or Raney nickel, is used.

Meanwhile, many heterogeneous hydrogenation catalysts for gas-phase or liquid-phase processes have been proposed and actively used in the industrial field, which convert esters, carbonyl compounds, or $C_4$ or more dicarboxylic esters such as alkylmalate and cyclohexane dicarboxylic ester into their corresponding monoalcohols, 1,4-butanediol, and 1,4-cyclohexanedimethanol, etc. Such ester-hydrogenating catalysts can be found in, for example, U.S. Pat. No. 5,406,004. There are disclosed various Cu-containing catalysts, for example, including Cu—$Al_2O_3$ catalysts, reduced CuO/ZnO-based catalysts (Cu:Zn=0.4:1~2:1), and reduced Cu-chromite-based catalysts (Cu:Cr=0.1:1~4:1). In addition, there are also disclosed several catalysts modified with Ba, Mn, rare-earth metals (for example, La, Sm, Th, Ce, Y, etc.), Mg or Ca for 0.1~15 wt % of the CuO/ZnO or Cu-chromite catalysts. Moreover, some catalysts further comprising, if necessary, carriers such as alumina or zirconia are also well known in the art. All of the above catalysts are commercially available. Further, there are also known Pd—Zn catalysts (see U.S. Pat. No. 5,185,476), Cu—$TiO_2$ catalysts (see U.S. Pat. No. 4,929,777), Re-Cu-Zn catalysts (see European Patent No. 373,946), Zn—Ru catalysts (see U.S. Pat. No. 4,443,649), and Pd, Pt or Ru-containing catalysts.

Even though a number of Cu-containing catalysts and noble metal-containing catalysts have been studied and developed for use in preparing alcohols from their corresponding carbonyl group-containing compounds, particularly from esters, there have been proposed few catalytic processes useful for preparation of 1,3-alkanediols from 3-hydroxyesters having a hydroxyl group in the specific β-position. WO 00/18712 discloses use of a Cu/ZnO-based catalyst in preparation of 1,3-propanediol from methyl 3-hydroxypropionate, but it was found to have no meaningful catalytic activity in consideration of industrial applicability.

U.S. Pat. No. 4,973,769 and WO 99/38613 describe Cu—$Al_2O_3$-based catalysts and Ru—Re-based catalysts, respectively, as catalysts to be used for preparing 1,2,4-butanetriol from malic acid or malic ester having a hydroxyl group in the β-position. In these references, however, relatively high pressure ranging from 100 to 300 atm is required as an essential reaction condition, so that these prior catalysts are unsuitable to be applied to a process for preparing the desired compounds of the present invention.

On the other hand, WO 00/18712 describes a method for hydrogenating methyl 3-hydroxypropionate to 1,3-propanediol in the presence of an alcohol solvent such as methanol. Although the alcohol solvent is expected to be able to suppress generation of lactones from 3-hydroxyesters and degradation of their ester groups, it is not helpful to maintain high selectivity at a high conversion rate and to ensure long-term reaction stability of the catalyst, since an alcohol having a low boiling point exists in the gas phase under the flow of $H_2$ gas in a fixed bed reactor. In fact, a significant decrease in the selectivity at a high conversion rate can be easily found in the Examples of the cited reference. Moreover, the boiling points and the other chemical properties of the reactants, i.e., hydroxyesters, and the products, i.e., 1,3-alkanediols, are so similar that isolation and purification of the product from the reactant are often difficult, which leads to problems in a practical process.

As compared with the hydrogenation of conventional esters, the hydrogenation process for 3-hydroxyesters substituted with a hydroxyl group at their β-position has numerous problems. The reactants are chemically and thermally so unstable that dehydration of the hydroxyl groups at their β-position can readily occur, and the resulting unsaturated esters are easily reduced to generate undesirable side products such as saturated esters or corresponding mono-alcohols wherein ester groups have been reduced. Additionally, β-lactone compounds generated from an intramolecular reaction of 3-hydroxyesters are thermally so unstable as to be degraded spontaneously or to form lactone polymers, and they are converted into additional side products including various esters and lactone compounds through intermolecular reactions with the other reactants or through condensation reaction with 1,3-alkanediols which are derived from hydrogenation of 1,3-hydroxyesters. The extent to which these side reactions occur is affected by reaction temperature, so there is a limit in controlling the reaction rate by increasing the reaction temperature.

However, keeping a high pressure in order to provide a moderate activity under a low temperature will also causes trouble in industrial application.

SUMMARY OF THE INVENTION

A feature of the present invention is to provide a novel process for preparing 1,3-alkanediols from 3-hydroxyesters, wherein a novel hydrogenation catalyst exhibiting high catalytic activity as well as high selectivity even under mild reaction conditions is employed.

According to one aspect of the present invention, there is provided a novel process for preparing 1,3-alkanediols from 3-hydroxyesters in a high yield, which comprises the steps of hydrogenating 3-hydroxyesters, for example in an alcohol-containing solvent, in the presence of a novel hydrogenation catalyst. The catalyst is prepared by adding an alkaline precipitator, such as an alkali metal carbonate or sodium hydroxide, to an aqueous solution containing a copper salt to form particles, and then aging the particles following the addition of colloidal silica thereto.

In more particular embodiments, the catalyst further includes at least one additional promoter selected from the group consisting of Re, Pd, Ru, Pt, Rh, Ag, Se, Te, Mo and Mn.

In further more particular embodiments, the catalyst is modified with one alkylsilane compound.

In more specific embodiments, the alcohol-containing solvent is a pure alcohol or a mixed solvent. In specific embodiments, the inventive process is carried out by a liquid-gas phase process in a mixed solvent including an alcohol and a high-boiling point solvent which boils at a higher temperature than the 1,3-alkanediol does. In other specific embodiments, the inventive process is carried out by a gas phase process in a low-boiling point alcohol solvent which boils at a lower temperature than the 1,3-alkanediol does.

According to another aspect of the present invention, there is provided a novel hydrogenation catalyst prepared according to the process set forth herein.

Other features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Priority Korean Patent Application Nos. 2000-71643, filed on Nov. 29, 2000, and 2001-33142, filed on Jun. 13, 2001, are incorporated herein in their entirety by reference.

According to the present invention, a Cu-containing catalyst stabilized with silica is employed in a hydrogenation process for preparing 1,3-alkanediols from 3-hydroxyesters. The major component of the catalyst is Cu in the form of an oxide, whose content in the catalyst is about 20 to about 99% by weight, preferably about 50 to about 95% by weight, and content of silica in the catalyst is about 1 to about 80% by weight, preferably about 5 to about 50% by weight. The silica-stabilized copper oxide catalyst as described above can be represented by $CUO-SiO_2$.

The catalyst of the present invention cannot be obtained by any of the typical impregnation processes using a conventional silica carrier, and thus it should be made by a particular method which comprises the steps of stabilizing micro-particles (diameter $\leq 10$ nm) of copper oxide precursor with silica in order to achieve the desired high catalytic activity. More specifically, the catalyst used in the present invention is prepared by a novel method which comprises the steps of adding an alkaline precipitator, such as an alkali metal carbonate or sodium hydroxide, to an aqueous solution containing a copper salt, and then aging the resulting copper hydroxide particles with colloidal silica. Significantly, the silica contained in the catalyst of the present invention acts as an essential component, and therefore it is clearly discriminated from the conventional carriers.

In the present invention, any of the conventional extruding or pelleting methods and impregnating methods using thermal-resistant carriers can be employed in forming the catalyst. The formed catalyst is then calcined for about 2 to about 10 hrs at a temperature ranging from about 200 to about 800° C., preferably about 300 to about 700° C.

The oxide catalyst thus obtained preferably can be used after activation with hydrogen or hydrogen-containing gas at a temperature ranging from about 150 to about 450° C. for about 1 to about 20 hours. In general, this activation step is performed while flowing the hydrogen or hydrogen-containing gas diluted with nitrogen or argon gas into a reactor filled with the calcined oxide catalyst. At this time, the concentration of hydrogen, the flow rate of the input gas, and the rate of temperature increase, etc., should be carefully controlled in order to prevent the catalyst from being sintered by heat generated in the course of its reduction.

The hydrogenation catalyst can be used in combination with one or more promoters in order to improve its hydrogenation activity and selectivity. As useful promoters, Re, Ru, Pd, Pt, Rh, Ag, Se, Te, Mo and Mn are preferred, and their content in the catalyst in general is about 0.001 to about 10 mol %, preferably about 0.003 to about 7 mol % based on Cu.

Alternatively, the hydrogenation catalyst of the present invention can be used after modification using alkylsilane compounds in order to improve its catalytic activity and selectivity. By modification of the hydrogenation catalyst, the Si—OH group of the catalyst and alkylsilane compounds are chemically bonded to form Si—O—Si bonds. Accordingly, the Si—OH groups in the catalyst are effectively masked in order to reduce the level of acidity. At this time, hydroxyl groups of silica are masked with the alkylsilane compounds. In the present invention, trialkoxymonoalkylsilane, dialkoxydialkylsilane or monoalkoxytrialkylsilane, wherein the alkyl group(s) include 1 to 30 carbon atoms, and each of the alkoxy groups is independently a linear or branched alkoxy group, preferably methoxy or ethoxy group, is used as the alkylsilane compound. Preferred alkylsilane compounds include, without limitation, trimethoxypropylsilane, trimethoxyoctylsilane, dimethoxydimethylsilane, dimethoxymethylpropylsilane, dimethoxymethyloctylsilane, methoxytrimethylsilane, methoxydimethylpropylsilane and methoxydimethyloctylsilane.

3-hydroxyesters used in the hydrogenation reaction according to the present invention can be represented by the following formulas (I) or (II):

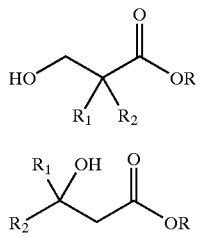

(I)

(II)

In the above formulas (I) and (II), $R_1$, $R_2$ and R are independently a hydrogen atom, a $C_{1-20}$ non-branched saturated aliphatic hydrocarbon, a $C_{3-20}$ branched aliphatic hydrocarbon, a $C_{5-20}$ saturated cyclic hydrocarbon, or a $C_{6-20}$ hydrocarbon chain containing a ring structure, each of which can be unsubstituted or substituted with an ester, hydroxyl or alkoxy group in place of a hydrogen atom at one or more carbon chains thereof.

In the above formulas (I) and (II), R of the ester group is preferably methyl, ethyl, n-propyl, isopropyl, n-butyl, isobutenyl, t-butyl, cyclohexyl, or cyclohexanemethyl.

Preferred examples of the 3-hydroxyesters include, without limitation, methyl (or ethyl) 3-hydroxypropionate, 3-hydroxybutyric ester, 3-hydroxypentanoic ester, 3-hydroxyhexanoic ester, 3-hydroxyheptanoic ester, 3-hydroxyoctanoic ester, 3-hydroxynonanoic ester, 3-hydroxydecanoic ester, 2-methyl-3-hydroxypropanoic ester, 2-methyl-3-hydroxybutanoic ester, 2-methyl-3-hydroxypentanoic ester, 2-methyl-3-hydroxyhexanoic ester, 2-methyl-3-hydroxyheptanoic ester, 2-methyl-3-hydroxyoctanoic ester, 2-methyl-3-hydroxynonanoic ester, 2-methyl-3-hydroxydecanoic ester, 2-ethyl-3-hydroxybutanoic ester, 2-ethyl-3-hydroxypentanoic ester, 2-ethyl-3-hydroxyhexanoic ester, 2-ethyl-3-hydroxyheptanoic ester, 2-ethyl-3-hydroxyoctanoic ester, 2-ethyl-3-hydroxynonanoic ester, 2-ethyl-3-hydroxydecanoic ester, etc.

According to the present invention, any type of the conventional hydrogenation processes, such as a liquid-phase slurry process, a liquid-gas phase process, and a gas-phase process, can be used in preparing 1,3-alkanediols from the 3-hydroxyesters by using a hydrogenation catalyst of the present invention.

According to the process of the present invention, it is possible to directly supply 3-hydroxyesters together with $H_2$ gas to the hydrogenation catalyst. However, it is much preferred to supply 3-hydroxyesters dissolved in an alcohol solvent or a mixed solvent consisting of an alcohol and a high-boiling point solvent whose boiling point is higher than those of the reactant and the product. This is in light of the facts that: (i) side reactions including intramolecular reaction of the reactant, i.e., 3-hydroxyesters, and generation of lactones or condensation reactions between the reactant and the product can be suppressed, (ii) catalytic activity and selectivity of the catalyst can be enhanced by controlling the concentration of the reactant to contact the catalyst during the reaction, and (iii) significant decrease of selectivity at a high conversion rate can be relieved.

Particularly for the liquid-gas phase process, 3-hydroxyesters are supplied dissolved in a mixed solvent consisting of an alcohol and a high-boiling point solvent as described above. At this time, the alcohol and the high-boiling point solvent preferably are mixed together in the ratio of about 5:95 to about 90:10 (w/w), more preferably about 10:90 to about 70:30 (w/w), and the final concentration of 3-hydroxyesters in the whole reaction mixture preferably is about 2 to about 95%, more preferably about 5 to about 90% by weight.

According to the liquid-gas phase process, the hydrogenation catalyst is filled in a reactor, for example a fixed bed reactor, and then both $H_2$ gas having a relatively low partial pressure and the 3-hydroxyester-containing solution are flowed simultaneously in the same direction into the reactor, so that $H_2$ gas may react with liquid-phase 3-hydroxyesters. This process is preferred in that retention time can be easily controlled.

As for the desirable reaction conditions for such liquid-gas phase processes, the reaction temperature preferably ranges from about 100 to about 250° C., more preferably about 120 to about 200° C., and the reaction pressure preferably ranges from about 50 to about 3,000 psig, more preferably about 150 to about 2,000 psig. Further, the flow rate of the 3-hydroxyester-containing solution into the reactor preferably is controlled so that LHSV preferably is in the range of about 0.01 to about 5 $hrs^{-1}$, more preferably about 0.03 to about 3 $hrs^{-1}$ when calculated for only the 3-hydroxyesters. The amount of $H_2$ gas preferably is also controlled so that molar ratio of $H_2$ to 3-hydroxyesters preferably is in the range of about 10 to about 300:1, more preferably about 20 to about 200:1.

Alternatively, when 3-hydroxyesters are hydrogenated by the gas-phase process, they are preferably supplied as being dissolved in an alcohol solvent. At this time, the mixing ratio of the 3-hydroxyesters and the alcohol solvent preferably is in the range of about 10:90 to about 90:10 (w/w), more preferably about 30:70 to about 70:30 (w/w).

According to the gas phase process, the hydrogenation catalyst is filled in a reactor, for example a fixed bed reactor, and then both $H_2$ gas having a relatively high partial pressure and the 3-hydroxyester-containing solution are flowed simultaneously in the same direction into the reactor, so that the 3-hydroxyesters, in an evaporated state, may react with $H_2$ gas.

As for the desirable reaction conditions for such gas phase processes, the reaction temperature preferably ranges from about 130 to about 200° C., more preferably about 140 to about 200° C., and the reaction pressure preferably ranges from about 100 to about 3,000 psig, more preferably about 200 to about 1,500 psig. Further, the flow rate of the 3-hydroxyester-containing solution into the reactor is controlled so that LHSV preferably is in the range of about 0.02 to about 1.0 $hrs^{-1}$, more preferably about 0.05 to about 0.20 $hrs^{-1}$ when calculated for only the 3-hydroxyesters. The amount of $H_2$ gas is also controlled so that molar ratio of $H_2$ to 3-hydroxyesters preferably is in the range of about 300 to about 3,000:1, more preferably about 500 to about 1,500:1. The gas phase process performed under these conditions would result in a very high conversion rate up to 99% or more without decrease of selectivity.

The alcohol which can be used in the above processes is not limited to a specific alcohol, but $C_{1-5}$ linear or non-linear alcohols, such as methanol, ethanol, propanol, isopropanol, n-butanol, isobutanol, t-butanol, etc., are preferred. A low-boiling point alcohol such as methanol, which boils a lower temperature than the 1,3-alkanediol does, is preferred particularly for the gas-phase process.

As the high-boiling point solvent, any solvent can be used, provided that it can be readily mixed with the 3-hydroxyester compound and has a boiling point higher than that of the 1,3-alkanediol so that it can be readily separated therefrom. However, it is preferable to use an ether compound such as tetra(ethylene glycol)dimethyl ether (hereinafter, referred to as "TEGDME"), penta(ethylene glycol)dimethyl ether or sulfolane.

While preparing 1,3-alkanediols from 3-hydroxyesters in the presence of the hydrogenation catalyst of the present invention, the reaction condition preferably is appropriately controlled so that conversion rate per pass is maintained in the range of about 30 to about 99%, more preferably about 60 to about 98%, and very preferably about 80 to about 98%. If the reaction is carried out under a stringent condition for maintaining the conversion rate over about 99%, the selectivity of the reaction will decrease, which is undesirable. In order to increase the conversion rate, various methods, for example, including a method wherein a part of the reaction product is isolated and successively recirculated without any additional separate purification step, and a method wherein the reaction product is isolated and purified, and then both unreacted 3-hydroxyesters and side products derived from transesterification are recirculated to the hydrogen reaction, may be adopted.

The present invention can be more clearly understood with referring to the following examples. It should be understood that the following examples are not intended to restrict the scope of the present invention in any manner.

EXAMPLE 1

(1) Preparation of a Hydrogenation Catalyst CuO(70 wt %)—SiO$_2$(30 wt %)

To a solution containing 60.0 g of [Cu(NO$_3$)$_2$.3H$_2$O] in 400 ml of distilled water was added 124 ml of aqueous NaOH solution (16 wt %) to form precipitates. Next, 21.2 g of colloidal aqueous silica solution, Ludox AS-40 (ammonium-stabilized type, 40 wt % of silica) was added thereto, and then the precipitates were allowed to age at about 70–80° C. for 4 hrs. The precipitates were recovered by filtration, washed with deionized water, and then dried at 120° C. for 12 hrs. Then, the catalyst powder thus obtained was shaped by pressing and crushed again into particles of about 20–40 mesh size. The catalyst particles were calcined at 450° C. under air atmosphere for 6 hrs. The calcined copper oxide catalyst was analyzed by XRD (XRD line broadening method), and the crystal size and BET surface area of the copper oxide were found to be 4.5 nm and 172 m$^2$/g, respectively.

(2) Activation of the Catalyst

In a tube-shaped reactor (1.27 cm in external diameter, 25 cm in length), the copper oxide catalyst (3.0 g) obtained from the above was filled, and then the temperature of the reactor was elevated to 300° C. at a rate of 0.5° C./min while flowing 5% H$_2$/N$_2$ mixed gas thereto. Then, the catalyst was reduced at 300° C. for 6 hrs.

(3) Hydrogenation Reaction of methyl 3-hydroxypropionate

After activating the catalyst by reduction as described above, the temperature of the reactor was cooled to 150° C., and the pressure in the reactor was adjusted to 900 psig. Then, H$_2$ gas was flowed into the reactor at a rate of 90 ml/min, and a reactant mixture consisting of methyl 3-hydroxypropionate (MHP):methanol:TEGDME= 20:20:60 (w/w/w) was introduced thereto via a HPLC pump at a flow rate of 0.015 ml/min in the same direction as that of the H$_2$ gas. The resulting product was sampled under the pressurized condition at intervals and subjected to GC analysis. After 50 hrs from initiation of the reaction, the conversion rate of MHP was 90.26% and the selectivity for 1,3-propanediol was 88.51%.

COMPARATIVE EXAMPLE 1

The procedure of Comparative Example 1 was conducted according to the same manner as in the above Example 1(3), except that a reactant mixture consisting of methyl 3-hydroxypropionate (MHP):methanol=20:80 (w/w) was used instead of that consisting of methyl 3-hydroxypropionate (MHP):methanol:TEGDME= 20:20:60 (w/w/w). In this reaction, the conversion rate of MHP was 81.21% and the selectivity for 1,3-propandiol was 74.60%.

EXAMPLE 2

A hydrogenation catalyst, CuO(80 wt %)—SiO$_2$(20 wt %), was prepared according to the same manner as in the above Example 1(1). To 10 g of the catalyst powder calcined at 450° C. was added a solution containing 0.163 g of Re$_2$O$_7$ in acetone, and then the catalyst powder was subjected to ball-milling. Then, the acetone was vaporized at room temperature, and the remaining powder was further dried at 120° C. The dried catalyst powder was shaped by pressing and crushed again into particles of about 20–40 mesh size. In a reactor, 3.0 g of the resulting catalyst particles were filled and reduced at 200° C. according to the same manner as in the above Example 1(2), except that pure H$_2$ gas, not H$_2$/N$_2$ mixed gas, was introduced into the reactor. With use of the thus-activated catalyst further comprising Re as a promoter, the hydrogenation reaction was performed under the condition as described in the following Table 1. The results are summarized in Table 1.

EXAMPLES 3–8

A hydrogenation catalyst, CuO(80 wt %)—SiO$_2$(20 wt %), was prepared according to the same manner as in the above Example 1(1), but was primarily calcined at 300° C. Then hydrogenation catalysts further comprising Pd, Ru, Ag, Se, Te or Mo as a promoter were prepared according to the same manner as in the above Example 2, but with variation of the precursor compound for the corresponding promoter as follows: Pd(NO$_3$)$_2$.2.5H$_2$O dissolved in distilled water was used as the Pd precursor; Ru$_3$(CO)$_{12}$ dissolved in ethanol was used as the Ru precursor; and each of AgNO$_3$, (NH$_4$)$_2$SeO$_4$, (NH$_4$)$_2$TeO$_4$ and (NH$_4$)$_6$Mo$_7$O$_{24}$.4H$_2$O dissolved distilled water was used as the Ag, Se, Te and Mo precursors, respectively. Each of the resulting catalysts was dried at 120° C., and then calcined at 450° C. for 6 hrs. The calcined catalysts were activated by reduction as described in Example 1(2). Hydrogenation reactions were conducted under the conditions as described in the following Table 1. The results are summarized in Table 1.

EXAMPLE 9

A hydrogenation catalyst, Mn$_{0.61}$Cu$_{10}$SiO$_2$, was prepared in the same manner as in the above Example 1(1), but with addition of an aqueous NaOH solution to an aqueous solution containing both Cu(NO$_3$)$_2$.3H$_2$O and Mn(NO$_3$)$_2$.6H$_2$O to form co-precipitates. The resulting catalyst was activated as described in Example 1(2), and then a hydrogenation reaction was conducted under the conditions as described in the following Table 1. The results are summarized in Table 1.

TABLE 1

| | Catalyst[1] | Temp. (° C.) | Pressure (psig) | Rate of supplying $H_2$ gas (ml/min) | Rate of supplying reactants[2] (ml/min) | Conversion Rate of MHP (%) | Selectivity for 1,3-propanediol (%) |
|---|---|---|---|---|---|---|---|
| Example 2 | $Re_{0.067}Cu_{10}SiO_2$ | 150 | 900 | 90 | 0.015 | 94.1 | 88.12 |
| Example 3 | $Pd_{0.040}Cu_{10}SiO_2$ | 150 | 1,000 | 90 | 0.015 | 94.86 | 89.63 |
| | | 155 | 1,000 | 90 | 0.020 | 91.97 | 88.36 |
| Example 4 | $Ru_{0.038}Cu_{10}SiO_2$ | 150 | 1,000 | 90 | 0.015 | 97.06 | 85.72 |
| | | 155 | 1,000 | 90 | 0.020 | 92.98 | 87.37 |
| | | 155 | 1,000 | 90 | 0.025 | 85.42 | 88.08 |
| Example 5 | $Ag_{0.022}Cu_{10}SiO_2$ | 155 | 900 | 90 | 0.015 | 96.70 | 84.28 |
| Example 6 | $Se_{0.018}Cu_{10}SiO_2$ | 150 | 1,000 | 90 | 0.015 | 92.03 | 87.04 |
| Example 7 | $Te_{0.013}Cu_{10}SiO_2$ | 150 | 1,000 | 90 | 0.015 | 94.81 | 87.33 |
| Example 8 | $Mo_{0.07}Cu_{10}SiO_2$ | 150 | 1,000 | 90 | 0.0175 | 92.55 | 88.01 |
| | | 155 | 1,000 | 90 | 0.0175 | 97.92 | 88.43 |
| Example 9 | $Mn_{0.61}Cu_{10}SiO_2$ | 150 | 1,000 | 90 | 0.0175 | 96.69 | 88.78 |
| | | 145 | 1,000 | 90 | 0.0175 | 82.90 | 87.70 |

[1]The subscripts represent atomic ratios between the promoters and Cu.
[2]MHP:MeOH:TEGDME = 20:20:60 (w/w/w)

EXAMPLE 10

A hydrogenation catalyst, CuO(80 wt %)—$SiO_2$(20 wt %), was prepared in the same manner as in the above Example 1(1). Next, 10.0 g of the catalyst powder calcined at 450° C. for 6 hrs was suspended in toluene under an argon atmosphere, and then 1.5 g of trimethoxyoctylsilane was added thereto. Then the reaction was conducted for 2 hrs with refluxing toluene, and the resulting catalyst powder was rinsed with toluene and dried. The dried catalyst powder was shaped by pressing and crushed again into particles of about 20–40 mesh size. In a reactor, 3.0 g of the catalyst particles were filled and primarily reduced with 5% $H_2/N_2$ mixed gas while the temperature of the reactor was slowly elevated to 200° C. Then, $H_2$ gas was introduced into the reactor to 900 psig, the temperature of the reactor was adjusted to 150° C., and then the hydrogenation reaction was performed under the same condition as described in Example 1(3). The results are summarized in the following Table 2.

TABLE 2

| Rate of supplying reactants[1] (ml/min) | Rate of supplying $H_2$ gas (ml/min) | Temperature (° C.) | Pressure (psig) | Conversion rate of MHP (%) | Selectivity for 1,3-propanediol (%) |
|---|---|---|---|---|---|
| 0.015 | 90 | 150 | 950 | 97.41 | 87.50 |
| 0.017 | 90 | 150 | 1,000 | 98.29 | 87.15 |
| 0.0185 | 90 | 150 | 1,000 | 94.72 | 88.86 |
| 0.0225 | 90 | 155 | 1,000 | 98.24 | 86.26 |
| 0.025 | 90 | 155 | 1,000 | 95.39 | 86.23 |

[1]MHP:MeOH:TEGDME = 20:20:60 (w/w/w)

EXAMPLE 11

A hydrogenation catalyst, CuO(80 wt %)—$SiO_2$(20 wt %), was prepared in the same manner as in the above Example 1(1). In a reactor, 3.0 g of the catalyst were filled, and then activated by reduction as described in Example 1(2). The hydrogenation reaction was carried out by using the activated catalyst as follows: $H_2$ gas was flowed into the reactor at a rate of 90 ml/min to 1000 psig at 155° C., and a reactant mixture consisting of methyl 3-hydroxybutyrate (MHB):methanol:TEGDME=20:20:60 (w/w/w) was introduced thereto at a flow rate of 0.015 ml/min in the same direction as that of $H_2$ gas. As a result, it was found that the conversion rate of MHB was 2.85% and the selectivity for 1,3-butanediol was 74.35%.

EXAMPLE 12

A hydrogenation catalyst, CuO—Mn—SiO$_2$, was prepared and reduced in the same manner as in the above Example 9. Then hydrogenation reactions were conducted under the different conditions as described in the following Table 3, while flowing a reactant mixture consisting of methyl 3-hydroxypropionate(MHP):methanol=40:60 (w/w) into a reactor filled with the catalyst. The results are summarized in Table 3.

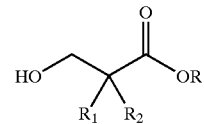

(I)

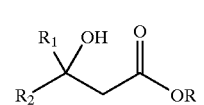

(II)

TABLE 3

| | Reaction condition | | | Conversion | Selectivity (%) | | | |
|---|---|---|---|---|---|---|---|---|
| Temperature (° C.) | Pressure (psig) | LHSV (hr$^{-1}$) | H$_2$/MHP (mol/mol) | rate of MHP (%) | PDO | 1-Propanol | Methyl propionate | Other products |
| 155 | 600 | 0.096 | 900 | 98.77 | 88.79 | 7.23 | 2.29 | 1.69 |
| 155 | 600 | 0.107 | 810 | 97.46 | 89.12 | 6.04 | 2.32 | 2.52 |
| 153 | 750 | 0.107 | 850 | 99.13 | 89.07 | 6.61 | 2.80 | 1.52 |
| 153 | 750 | 0.096 | 950 | 99.35 | 89.06 | 6.74 | 2.55 | 1.11 |
| 160 | 450 | 0.129 | 670 | 95.08 | 85.98 | 7.71 | 3.72 | 2.59 |
| 160 | 600 | 0.129 | 670 | 97.94 | 86.07 | 8.0 | 3.54 | 2.39 |

The present invention provides a novel process for preparing 1,3-alkanediols through hydrogenating 3-hydroxyesters. According to the process of the present invention, by employing a unique hydrogenation catalyst in a certain reaction system, 1,3-alkanediols can be selectively produced in a high yield.

What is claimed is:

1. A process for preparing a 1,3-alkanediol from a 3-hydroxyester, which comprises the step of hydrogenating a 3-hydroxyester in the presence of a catalyst prepared by adding an alkaline precipitator to an aqueous solution containing a copper salt to form particles and then aging the particles following the addition of colloidal silica thereto.

2. The process according to claim 1, wherein the alkaline precipitator is an alkali metal carbonate or sodium hydroxide.

3. The process according to claim 1, wherein the catalyst comprises CuO and SiO$_2$ in the ratio of about 9:1 to about 5:5 by weight.

4. The process according to claim 1, wherein the catalyst further comprises at least one additional promoter selected from the group consisting of Re, Pd, Ru, Pt, Rh, Ag, Se, Te, Mo and Mn in an amount from about 0.001 to about 10 mol % based on Cu.

5. The process according to claim 1, wherein the catalyst is modified with one alkylsilane compound selected from the group consisting of trialkoxymonoalkylsilane, dialkoxydialkylsilane and monoalkoxytrialkylsilane, wherein each alkyl group includes 1 to 30 carbon atoms, and wherein each alkoxy group is independently a linear or branched alkoxy group.

6. The process according to claim 5, wherein each alkoxy group is independently a methoxy or ethoxy group.

7. The process according to claim 1, wherein the 3-hydroxyester is represented by the following formulas (I) or (II):

wherein R$_1$, R$_2$ and R are independently a hydrogen atom, a C$_{1-20}$ non-branched saturated aliphatic hydrocarbon, a C$_{3-20}$ branched aliphatic hydrocarbon, a C$_{5-20}$ saturated cyclic hydrocarbon, or a C$_{6-20}$ hydrocarbon chain containing a ring structure, each of which can independently be unsubstituted or substituted with an ester, hydroxyl or alkoxy group in place of a hydrogen atom at one or more carbon chains thereof.

8. The process according to claim 7, wherein in formulas (I) and (II), R is methyl, ethyl, n-propyl, isopropyl, n-butyl, isobutenyl, t-butyl, cyclohexyl, or cyclohexanemethyl.

9. The process according to claim 7, wherein the 3-hydroxyester is methyl 3-hydroxypropionate.

10. The process according to claim 1, wherein the hydrogenation reaction is carried out by a liquid-gas phase process in a mixed solvent comprising an alcohol and a high-boiling point solvent which boils at a higher temperature than the 1,3-alkanediol does.

11. The process according to claim 10, wherein the high-boiling point solvent is selected from the group consisting of tetra(ethylene glycol)dimethyl ether, penta(ethylene glycol)dimethyl ether and sulfolane, and wherein the weight ratio of the alcohol to the high-boiling point solvent ranges from about 5:95 to about 90:10 (w/w).

12. The process according to claim 10, wherein the 3-hydroxyester is dissolved in the mixed solvent to a concentration of about 2 to about 95% by weight.

13. The process according to claim 10, wherein the hydrogenation reaction is carried out at a temperature of about 100 to about 250° C. under a pressure of about 50 to about 3,000 psig in a fixed bed reactor.

14. The process according to claim 13, wherein the hydrogenation reaction is carried out while maintaining the molar ratio of the introduced H$_2$ gas to the 3-hydroxyester in the range from about 10:1 to about 300:1 (m/m).-

15. The process according to claim 1, wherein the hydrogenation reaction is carried out by a gas phase process in a low-boiling point alcohol solvent which boils at a lower temperature than the 1,3-alkanediol does.

16. The process according to claim 15, wherein the low-boiling point alcohol solvent is methanol.

17. The process according to claim 15, wherein the weight ratio of the 3-hydroxyester to the alcohol solvent ranges from about 10:90 to about 90:10 (w/w).

18. The process according to claim 15, wherein the hydrogenation reaction is carried out at a temperature of about 130 to about 200° C. under a pressure of about 100 to about 3,000 psig in a fixed bed reactor.

19. The process according to claim 18, wherein the hydrogenation reaction is carried out while maintaining the molar ratio of the introduced $H_2$ gas to the 3-hydroxyester in the range from about 300:1 to about 3,000:1 (m/m).

* * * * *